US00PP08384P

United States Patent [19]

Akerboom

[11] Patent Number: Plant 8,384

[45] Date of Patent: Sep. 21, 1993

[54] ASTER PLANT NAMED LILAC BLUE ADMIRAL

[76] Inventor: Petrus J. F. Akerboom, Paradijsweg 61, 2461 TL, Ter Aar, Netherlands

[21] Appl. No.: 895,727

[22] Filed: Jun. 9, 1992

[51] Int. Cl.[5] ..... A01H 5/00
[52] U.S. Cl. ..... Plt./68.1
[58] Field of Search ..... Plt./68.1

*Primary Examiner*—James R. Feyrer
*Attorney, Agent, or Firm*—Foley & Lardner

[57] ABSTRACT

A distinct cultivar of Aster plant named 'Lilac Blue Admiral', characterized by its cupped capitulum form and daisy capitulum type, bluish-purple ray florets, yellow green disc florets, strong well-branched flower stems, and its numerous flowers borne on short pedicels.

1 Drawing Sheet

The present invention comprises a new and distinct cultivar of Aster L. hereinafter referred to by the cultivar name 'Lilac Blue Admiral'.

'Lilac Blue Admiral' is a product of a planned breeding program which had the objective of creating new perennial Aster cultivars for year-round commercial production having, among other features, good flower (capitulum) form and shape, and having superior vase-life lasting quality of the cut flowers. The specifically named traits in combination were not present in previously available commercial cultivars prior to the Aster Butterfly series of earlier varieties of the present invention and for which plant patents have been granted. The cultivars 'White Butterfly', 'Blue Butterfly', 'Rose Butterfly' and 'Pink Butterfly' are covered by U.S. Plant Pat. Nos. 7,397; 7,399; 7,400; and 7,401, respectively.

'Lilac Blue Admiral' was originated from a hybridization made by the inventor P. Akerboom in a controlled breeding program in Ter Aar, The Netherlands, in 1987. The female parent of 'Lilac Blue Admiral' was an unnamed *Aster novi-belgii* seedling. The male parent was an unnamed *Aster novi-pilosus* seedling.

'Lilac Blue Admiral' was discovered and selected as one flowering plant within the progeny of the stated parentage by the inventor P. Akerboom on Sep. 10, 1987 in a controlled environment in Ter Aar and identified as seedling No. 87.M.K.B.Bl.6.G.

The first act of asexual reproduction of 'Lilac Blue Admiral' was accomplished when vegetative cuttings were taken from the initial selection in November 1987 in a controlled environment in Ter Aar by a technician working under formulations established and supervised by P. Akerboom.

Horticultural examination of selected units initiated in 1988 and 1989 has demonstrated that the unique combination of characteristics as herein disclosed for 'Lilac Blue Admiral' are firmly fixed and are retained through successive generations of asexual reproduction.

'Lilac Blue Admiral' has not been observed under all possible environmental conditions. The phenotype may vary significantly under different environmental conditions of temperature, light intensity and daylength, without, however, any variance in the genotype.

The following observations, measurements and comparisons describe plants grown in Ter Aar, The Netherlands, under greenhouse conditions which approximate those generally used in commercial greenhouse practice in this country. The following traits have been repeatedly observed and are determined to be basic characteristics of 'Lilac Blue Admiral', which, in combination, distinguish this Aster as a new and distinct cultivar:

1. Cupped capitulum form.
2. Daisy capitulum type.
3. Bluish-purple ray floret color.
4. Diameter across the face of capitulum of 32 to 35 mm at maturity.
5. Strong, well branched flower stems.
6. Many capitula per synflorescence, borne on short pedicels.

The accompanying color photographic drawings show typical synflorescence of 'Lilac Blue Admiral', with the colors being as nearly true as possible with illustrations of this type.

The photograph at the top of the sheet is a perspective view of 'Lilac Blue Admiral' grown as a single stem cut spray Aster.

The photograph at the bottom is a top view of several mature flowers.

Of the commercial cultivars known to the inventor, the most similar to 'Lilac Blue Admiral' is the variety 'Blue Butterfly', disclosed in U.S. Plant Pat. No. 7,399. Reference is made to attached Chart A, which compares certain characteristics of 'Lilac Blue Admiral' to the same characteristics of 'Blue Butterfly'.

In comparison to 'Blue Butterfly', 'Lilac Blue Admiral' has more vigorous growth, thicker and courser flower stems, shorter and broader leaves, larger flowers (capitula) of a pale purplish color, and many more ray florets. Similar traits are capitulum form and type, spray formation, photoperiodic light reaction, and equally long lasting vase-lifes.

When compared to the male parent's flower and flower stem characteristics, 'Lilac Blue Admiral' is much easier to handle during harvesting. *Novi-belgii* cultivars typically have brittle and easy breaking flower heads and branching stems. 'Lilac Blue Admiral' is absolutely free of these drawbacks.

In the following description color references are made to The Royal Horticultural Society Colour Chart. The color values were determined between 12:00 and 14:00 hours on Jun. 20, 1989 at Ter Aar, The Netherlands.

Classification:

*Botanical.*—*Aster pilosus* × *novi-belgii* cv 'Lilac Blue Admiral'.

*Commercial.*—Medium daisy-like spray Aster perennial.

INFLORESCENCE

A. Capitulum:

*Form.*—Cupped.

*Type.*—Daisy.

*Diameter across face.*—32 to 35 mm.

*Arrangement.*—Raceme inflorescence.

B. Corolla of ray florets:

*Color (general tonality from a distance of three meters).*—Purplish.

*Color (upper surface).*—Closest to 76A.

*Color (under surface).*—Closest to 76A.

*Shape of floret.*—Apex rounded; elliptic; very long, straight.

*Size of floret.*—16–17 mm long×4–5 m wide.

*Number of ray florets.*—28–35.

C. Corolla of disc florets:

*Color (mature).*—Disc florets themselves are closest to 1C/1D; disc base is deeper yellow which gives overall deeper effect than floret color.

*Color (immature).*—Closest to 1C/1D.

*Diameter of disc.*—4–5 mm.

D. Reproductive organs.

*Androecium.*—Present on disc florets only; little to very little pollen.

*Gynoecium.*—Present on both ray and disc florets.

PLANT

A. General appearance:

*Height.*—Tall; depends on light reaction; under continuous long days it can grow up to two meters tall; medium to dense branching.

B. Foliage:

*Color.*—RHS 147A yellow-green.

*Shape.*—Oblanceolate; tip acute.

*Size.*—Lower leaves, length approximately 140 mm, short to very short; width 20 mm, broad. Upper leaves, length 60 mm; width 9 mm.

*Margin.*—Entire.

*Arrangement.*—Alternate, with angle acute.

CHART A
Comparison of 'Lilac Blue Admiral' and 'Blue Butterfly'

| Cultivar | LILAC BLUE ADMIRAL | BLUE BUTTERFLY |
|---|---|---|
| Ray floret color | Purplish-blue | Blue |
| Capitulum form and type | Cupped daisy | Cupped daisy |
| Spray formation | Compound | Compound |
| Pedicels | 5–40 mm long | 8–18 mm long |
| Diameter across face of capitulum | 32–35 mm | 27–30 mm |
| Number of ray florets | 28–35 | 27–29 |

I claim:

1. A new and distinct cultivar of Aster named 'Lilac Blue Admiral', as illustrated and described.

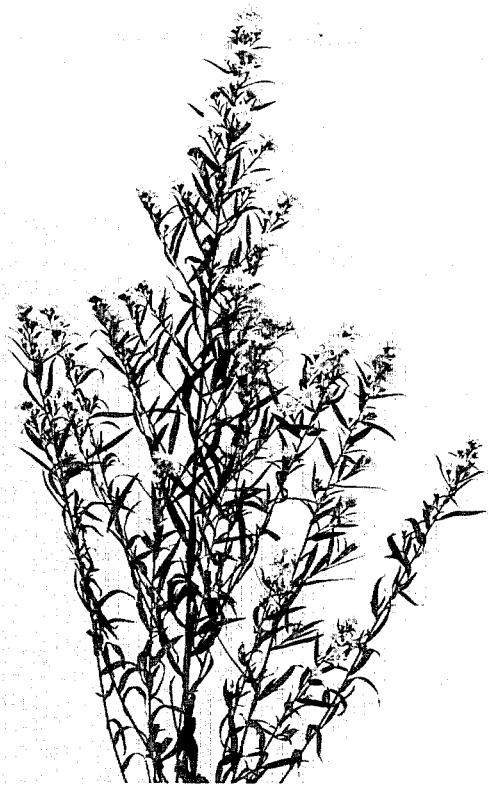
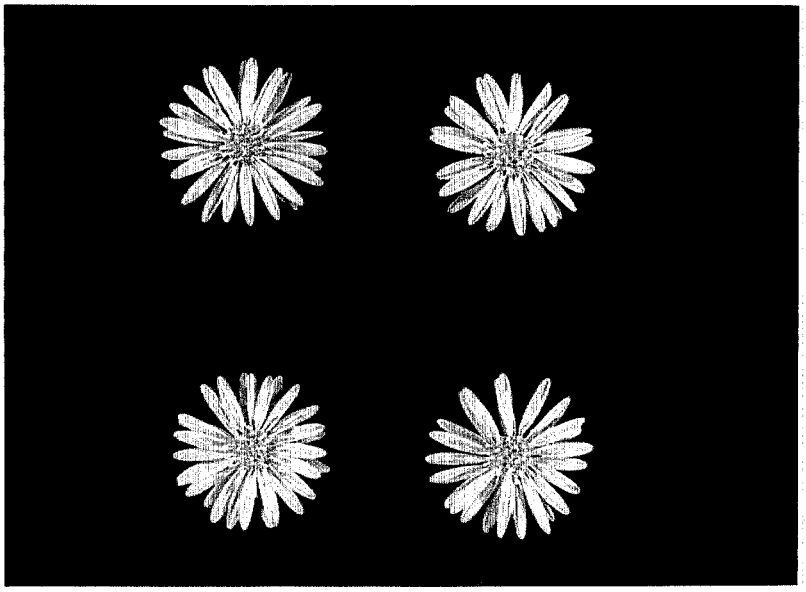

* * * * *